United States Patent
Bronshtein

(10) Patent No.: US 10,632,188 B2
(45) Date of Patent: Apr. 28, 2020

(54) COMPOSITIONS CONTAINING AMBIENT-TEMPERATURE STABLE, INACTIVATED BUT THERAPEUTICALLY ACTIVE BIOPHARMACEUTICALS AND METHODS FOR FORMULATION THEREOF

(71) Applicant: Universal Stabilization Technologies, Inc., San Diego, CA (US)

(72) Inventor: Victor Bronshtein, San Diego, CA (US)

(73) Assignee: UNIVERSAL STABILIZATION TECHNOLOGIES, INC., San Diego, CA (US)

( * ) Notice: Subject to any disclaimer, the term of this patent is extended or adjusted under 35 U.S.C. 154(b) by 0 days.

(21) Appl. No.: 15/638,937

(22) Filed: Jun. 30, 2017

(65) Prior Publication Data

US 2018/0125966 A1    May 10, 2018

Related U.S. Application Data

(62) Division of application No. 14/665,107, filed on Mar. 23, 2015, now Pat. No. 9,744,227.

(60) Provisional application No. 62/056,415, filed on Sep. 26, 2014.

(51) Int. Cl.

| *A61K 39/205* | (2006.01) |
| *A61K 9/14*   | (2006.01) |
| *C12N 7/00*   | (2006.01) |
| *A61K 35/744* | (2015.01) |
| *A61K 39/12*  | (2006.01) |
| *A61K 39/07*  | (2006.01) |
| *A61K 39/09*  | (2006.01) |
| *A61K 39/00*  | (2006.01) |

(52) U.S. Cl.
CPC ........... *A61K 39/205* (2013.01); *A61K 9/145* (2013.01); *A61K 35/744* (2013.01); *A61K 39/07* (2013.01); *A61K 39/09* (2013.01); *A61K 39/12* (2013.01); *C12N 7/00* (2013.01); *A61K 2039/5252* (2013.01); *A61K 2039/5254* (2013.01); *C12N 2760/20134* (2013.01); *C12N 2760/20161* (2013.01)

(58) Field of Classification Search
None
See application file for complete search history.

(56) References Cited

U.S. PATENT DOCUMENTS

| 2008/0229609 A1* | 9/2008  | Bronshtein | .......... A01N 1/0284  34/287 |
| 2013/0261372 A1* | 10/2013 | Hyde       | .......... A61M 31/002   600/9 |
| 2016/0089430 A1* | 3/2016  | Bronshtein | .......... A61K 39/09   424/224.1 |

OTHER PUBLICATIONS

Datta et al., Immunity, Jul. 2006, 25:143-152. (Year: 2006).*
Franka et al., Vaccine, 2009, 27:7149-7155. (Year: 2009).*

* cited by examiner

*Primary Examiner* — Stacy B Chen
(74) *Attorney, Agent, or Firm* — Coastal Patent Law Group, P.C.; Joshua S. Schoonover, Esq.

(57) ABSTRACT

The disclosure concerns compositions containing inactivated but therapeutically active biopharmaceuticals, and methods for formulation thereof. Biopharmaceuticals are encapsulated and immobilized in dry amorphous carbohydrate-glass and irradiated for inactivation while in the dry state. The resulting compositions provide ambient-temperature stable, therapeutically active but inactivated biopharmaceuticals for use in vaccines and other applications.

5 Claims, 3 Drawing Sheets

Survival of Vegetative Form of Anthrax Sterne Strain Vaccine After PBV Drying and Subsequent Storage at 37°C

Survival ($10^7$ CFU/mL) vs. Days Stored at 37°C (log scale)

FIG. 1

Metabolic Activity of Anthrax Vaccine (MTT Assay)

OD Output vs. Time After Reconstitution (min)

- No Radiation, No Dilution
- No Radiation, Dilution 1:3
- No Radiation, Dilution 1:9
- Radiated, No Dilution
- Radiated, Dilution 1:3
- Radiated, Dilution 1:9

FIG. 2

METHOD FOR PRODUCING THERMOSTABLE INACTIVATED
BUT THERAPEUTICALLY ACTIVE BIOPHARMACEUTICALS

PROVIDING ONE OR MORE BIOPHARMACEUTICALS, INCLUDING:
VIRUSES; BACTERIA; ARCHAEA; FUNGI; PROTISTA; PROTEINS; ANTIGENS;
OR A COMBINATION THEREOF;

↓

PRESERVING SAID BIOPHARMACEUTICALS IN A DRY CARBOHYDRATE GLASS;

↓

SAID PRESERVING INCLUDING:
VACUUM DRYING SAID BIOPHARMACEUTICALS
CONTAINED IN THE CARABOHYDRATE GLASS FOR
AT LEAST SIX HOURS AT 40°C OR A HIGHER TEMPERATURE
TO YIELD THERMOSTABLE BIOPHARMACEUTICALS; AND

↓

CHARACTERIZED BY THE METHOD FURTHER COMPRISING:
SUBSEQUENT TO PRESERVING THE BIOPHARMACEUTICALS,
IRRADIATING THE PRESERVED THERMOSTABLE BIOPHARMACEUTICALS
CONTAINED IN THE DRY CARBOHYDRATE GLASS USING A PERMEATED
IONIZING RADIATION DOSE OF AT LEAST 12.5 kGa.

*FIG.5*

COMPOSITIONS CONTAINING AMBIENT-TEMPERATURE STABLE, INACTIVATED BUT THERAPEUTICALLY ACTIVE BIOPHARMACEUTICALS AND METHODS FOR FORMULATION THEREOF

CROSS-REFERENCE TO RELATED APPLICATIONS

This application is a divisional of U.S. Ser. No. 14/665,107, filed Mar. 23, 2015, and titled "COMPOSITIONS CONTAINING AMBIENT-TEMPERATURE STABLE, INACTIVATED BUT THERAPEUTICALLY ACTIVE BIOPHARMACEUTICALS & METHODS FOR FORMULATION THEREOF";

which claims benefit of priority with U.S. Provisional Ser. No. 62/056,415, filed Sep. 26, 2014;

the contents of each of which are hereby incorporated by reference.

STATEMENT REGARDING FEDERALLY SPONSORED RESEARCH

This invention was made with government support under 5R44AI080035 awarded by the National Institute of Health (NIH). The government has certain rights in the invention.

BACKGROUND

Field of the Invention

This invention relates to ambient-temperature stable compositions containing biopharmaceuticals and methods for formulation thereof; and more particularly, to such ambient-temperature stable compositions containing inactivated but therapeutically active (IBTA) microorganisms, proteins, antigens, or a combination thereof.

Description of the Related Art

Definitions

For purposes of this document, the term "microorganisms" is intended to include: viruses; bacteria; archaea; fungi; protista, yeast, and the like.

The terms "vaccine", "biopharmaceutical", "biotherapeutic", "probiotic" and "biologic", are each interchangeable herein, and each is intended to be defined as a composition containing at least a portion or component of a biological source. Examples of biopharmaceuticals, for purposes of this document, include, but are not limited to: microorganisms, proteins, and antigens.

In addition, "biopharmaceuticals", "therapeutics", "vaccines" and "probiotics" are each intended to be interchangeable herein, and collectively may be generally defined as "biopharmaceuticals".

The term "inactivated but therapeutically active (IBTA) biopharmaceutical is interchangeable with the term "inactivated but potent vaccine" and "inactivated but immunologically active vaccines".

The term "vaccine potency" as used herein, includes: survival rate of microorganisms, therapeutic activity of biopharmaceuticals, vaccine immunological activity, enzymatic or other activity of proteins cytokines and other macromolecules. Survival yield of viruses and bacteria and other microorganism means the same and will be used to address a measure of specific positive quality of the biologicals to which the method of this invention will be applied or used.

The term "thermos-stability" is defined as stability at all ambient temperatures from −20° C. to +37° C., for at least a year, with loss in the potency during 1 year storage below 0.5 logs even at +37° C.

The terms "therapeutically active" and "immunologically active" are each interchangeable herein, and each is intended to be defined by the common definition in the art.

The terms "sterilized" and "inactivated" are each interchangeable herein, and each is intended to be defined by the common definition in the art.

The terms "preserved", "stabilized", and "immobilized" are each interchangeable herein, and each is intended to be defined by the common definition in the art.

The term carbohydrate glass includes: any glass comprising a carbohydrate, but may further comprise any of: buffers, salts, amino acids, polymeric protectants, or a combination thereof.

As used herein "ambient-temperature stable" when used in conjunction with "biopharmaceutical", "biologic", or "biotherapeutic" is defined as a composition containing at least a portion or component of a biological source that is immobilized in amorphous carbohydrate glass at ambient temperature (from −20° C. to 37° C.) to ensure ambient-temperature stability. The biopharmaceutical immobilized in carbohydrate glass is generally dried at temperatures above ambient, often by way of several drying steps, in order to yield sufficient stability at ambient temperature.

Finally, for purposes herein, the terms "immobilized", "preserved" and "stabilized" are used interchangeably, depending on whether the associated biopharmaceutical is a virus, bacteria, etc., and are intended to be defined by the common definition in the art.

Vaporization comprises three different processes, including: boiling, sublimation, and evaporation. Where sublimation is transformation from a crystallized into vapor gas phase. Boiling is a result of formation of vapor bubbles in the body of the superheated liquid. Superheating is necessary for the bubble nucleation for boiling to happen. Evaporating, also known as desorption, is transformation from liquid into vapor gas phase during which no boiling occurs and water molecules leave an aqueous liquid from its surface. Evaporation does not require an overheating.

Now describing the use of certain biopharmaceuticals as concerned herein within the context of their use as a therapeutic vaccine or other treatment platform.

Live Attenuated Vaccines (Virus and Bacteria)

It is well known that there can be a significant risk in administering live vaccines and other biopharmaceuticals containing microorganisms, even when attenuated.

Many conventional viral and bacterial vaccines are presently administered in a live attenuated state. These include attenuated pathogens used to treat the specific disease that they cause, and vectors for delivery of agents for gene therapy. A known risk of producing a live attenuated vaccine as opposed to an inactivated vaccine is the risk of reversion for virulence in the host. There is also a possibility for reaction to the production or attenuation process, such as, for example, egg allergy. Each vaccine released to the market for delivery in this state has been approved through clinical human trials to have a certain degree of safety in the general population, but there are often small subpopulations that are at a higher risk of negative response to the treatment. Immunocompromised individuals are at obvious risk for this response as they are often unable to fight off even slightly virulent biologicals. However, people are not always aware that they may have a weakened immune system, leaving a possibility of danger even in the typically-healthy patient. There are other factors such as genetic susceptibility that may leave certain groups of people more vulnerable to adverse vaccination responses. Effects can range from redness and swelling to mortality in some cases.

Probiotics

Other organisms with potential risk in certain populations include live probiotic bacteria. Historically defined by the World Health Organization (WHO) as "live microorganisms that, when administered in adequate amounts, confer a healthy benefit to the host"; these bacteria are meant to supplement the innate healthy flora and help to protect against pathogens. Protection occurs through various mechanisms. By 'crosstalk' between the bacteria and epithelial cells mediated by toll like receptors and small molecules, they are able to modulate both innate and adaptive mucosal immunity. Their adherent properties help to heal and maintain the tissues lining the digestive tract, sealing the tight junctions between the cells to reduce permeability. The typical dose of probiotic supplements number in the billions, but is only a small contribution to the trillions of bacterial cells in the human body. Large numbers of healthy bacteria protect against proliferation of pathogens in the body by competitive exclusion and by physical cell binding to facilitate pathogen elimination from the system. Prominent concerns with probiotics are in individuals with gastrointestinal disorders, chronic illness, immunocompromise, or in premature infants. Documented adverse reactions include sepsis, nonspecific or aggressive immune response, and endocarditis among others. Other potential side-effects are bacterial acquisition of virulence factors or resistance genes, the spread of those acquired factors to other intestinal bacterial populations, or translocation to blood or other tissues causing bacteremia.

Inactivated Vaccines

"Inactivated vaccines" are the most common example of killed therapeutically active microorganisms. Some of the most notable inactivated viral vaccines include Inactivated Poliovirus (IPV), Hepatitis A, inactivated rabies, and injectable seasonal influenza vaccines. Inactivated bacterial vaccines include those against typhoid, cholera, plague and pertussis. Vaccines of this type are typically created by subjecting cultured organisms to high heat, radiation, or chemicals such as formaldehyde or formalin. Because the replication components are destroyed there is no risk of genetic reversion to virulence as with live vaccines. However inactivation processes can be harsh on the organisms and inefficient, often destroying a large proportion of the immune-stimulating components. For example heat and chemical inactivation methods destroy not only the nucleic acids and ability of microorganisms to replicate, but also many epitopes, capsid proteins, intracellular and membrane associated proteins and other molecules relatively intact and recognizable by the immune system or responsible for other therapeutic activity. Inactivated vaccines appear to be more stable than live vaccines because the most fragile components that would normally be lost with time and temperature have already been inactivated, or because it is difficult to accurately evaluate losses biopharmaceutical potency or therapeutic functions in inactivated specimens. One drawback of non-replicating organisms is that they are less potent and have a shorter period of protection in the system, often requiring boosters to maintain immunity long-term. Another is that a larger dosage must be given to counter the proportion of destroyed organisms and the fact that they will not replicate to higher titers in the host.

In addition, development of ambient-temperature stable inactivated vaccines and other biotherapeutics is a challenge because in order to demonstrate stability of inactivated vaccines after preservation, animal immunogenicity studies (or therapeutic potency studies) must be run at each evaluation point. In this the embodiments disclosed herein, we suggest thermostabilizing (at ambient and higher temperatures) the biotherapeutic component first, and subsequently inactivating such by irradiation. This will allow testing and verifying survival (or activity) of preserved specimens over time before inactivation, without a need to conduct animal studies at each stability time point.

Killed Probiotics

'Killed probiotics' are increasing in popularity in various industries. Although they are typically administered alive so they have the ability to colonize the gut for prophylactic protection, an increasing number of studies have shown that various strains have a therapeutic effect when administered in an inactivated form. The mechanism of therapeutic action in this case is not yet fully elucidated. This approach to probiotic use has shown potential for use in the agriculture and livestock industry where widespread antibiotic use is often standard to stave off diseases prevalent in the overcrowded and unsanitary conditions. Protein components of the probiotic surface strongly aggregate to each other and adhere to the mucin and extracellular matrix materials of cells. When adhered to the mucin membrane of the intestine they create a barrier to block the pathogenic cells from attaching. They also function to adhere to the pathogens themselves, coating their attachment structures and flushing them out of the system.

Killed probiotic therapy uses a very large dose of bacteria to compensate for the fact that they will not replicate in the host, and the methods of killing are damaging to the cells. Most studies use harsh heat or chemical treatment to kill the cells which can be detrimental to the external proteins and epitopes which are used for adhesion and cellular recognition, therefore leaving a less potent therapy.

Therefore there is an urgent need in developing more gentle methods for inactivation of biotherapeutics and production of ambient-temperature stable inactivated vaccines and other biotherapeutics.

After many methods of production or purification of active biologicals including cytokines, toxins, therapeutic proteins or protein antigens from blood, cell cultures, milk, plant extracts or other biological liquids, the products could be contaminated with live microorganisms. We found that inactivation of contaminating microorganisms could be performed by irradiation of the active biologicals immobilized in carbohydrate glasses at AT without destroying their therapeutic activity (i.e. immunological activity of epitopes)

Stabilization Technologies

Currently, it is well recognized that the long-term stabilization of biologicals requires arresting molecular mobility to stop the degradation processes during storage. This can be achieved only by vitrification, which is the transformation from a liquid into a supercooled or supersaturated, noncrystalline, amorphous solid state, known as the "glass state". The basic premise is that the high viscosity of the glass state will arrest all diffusion-limited physical processes and chemical reactions, including the processes responsible for the degradation of biological materials. This premise is based on Einstein's theory that establishes the inverse proportionality between viscosity and molecular mobility (or diffusion coefficients of molecules). In general terms, glasses are thermodynamically unstable, amorphous materials; however, they can maintain the same state for long periods of time because of their very high viscosity ($10^{12}$-$10^{14}$ Pa*s); for example, a typical liquid has a flow rate of 10 m/s compared to $10^{14}$ m/s in the glass state.

Depending on the composition, a biological suspension could be transferred into the vitrified state, by cooling, increasing in hydrostatic pressure, or a combination thereof, at different temperatures, if the cooling rate is sufficiently high to avoid formation of the crystalline phase. For example, pure water could be vitrified by cooling below −148° C. Preservation of cells and other biologicals by cryo-vitrification has been introduced as an alternative to preservation by freezing to avoid freeze-induced damage of biologicals. To achieve cryo-vitrification before cooling cells are typically equilibrated in concentrated solutions of low toxicity polyols (protectors) like DMSO, glycerol, Ethylene Glycol, etc. These solutions help to avoid formation of ice crystals (freezing) but have very low glass transition temperatures ($T_g$), i.e., below −100° C., because of high water concentration and low $T_g$ of pure protectors. Therefore for preservation of biologicals above −100° C. one should use protectors with higher $T_g$.

In general the presence of water in a sample has a strong plasticizing effect, which decreases the glass transition temperature ($T_g$) and thus limits stability at higher temperatures (AT). For example, for water, $T_g$ is about −148° C., for 80% sucrose, $T_g$ is about −40° C.; $T_g$ of 99% sucrose is about +52° C. Therefore, if biologicals are to be preserved without degradation at an ambient temperature, they must be strongly dehydrated before transformed in the glass state by cooling. Similar to that for cryo-vitrification in the dry immobilized state, biopharmaceuticals are dormant, but can be returned to the active (or live) state after reconstitution with water.

Dehydration (drying) can be very damaging to vaccines and other fragile biologicals if performed in the absence of protective molecules (i.e. sucrose, trehalose, etc.) that adsorb at the surface of biological membranes and macromolecules and replace water of hydration at the surfaces, and this way protects the biologicals from destruction associated with hydration forces that arise during dehydration. Because of this, proper selection of the protective molecule is a key to a successful stabilization of biologicals at ambient temperatures without loss of their activity.

Evaporative Drying (Desorption)

A simple method of drying that can be applied for long-term stabilization of biologicals at ambient temperatures is an evaporative drying. During evaporation, water leaves a specimen from its surface into a dry air or vacuum. However, before reaching the surface water should diffuse through the body of the specimen. Thus, evaporative drying is a diffusion-limited process. Because of this, desorption could be applied only for drying of small drops or very thin specimens with large surface to volume ratios. After desorption, a specimen should be cooled to achieve the glass state.

Evaporative drying (ED) was very successfully applied for producing AT stable formulation of many biopharmaceuticals including vaccines. However, (ED) is very difficult to scale for most applications. Because of this, freeze-drying (FD) and spray-drying (SD) technologies are conventionally used as the primary methods for the stabilization of vaccines and fragile pharmaceuticals in the dry state. However, there were fundamental reasons preventing freeze-drying and spray-drying from delivering ambient-temperature stable vaccines and many other biologicals.

Freeze-Drying (Lyophilization)

Freeze-drying has been unsuccessful in delivering ambient-temperature stable vaccines.

Despite its limitations and shortcomings, freeze-drying has remained, for more than 50 years, the primary method to stabilize fragile biopharmaceuticals and biologics (vaccines, therapeutic proteins, probiotics, etc.) in the dry state. This is, in part, because of erroneous conventional belief that drying at low temperature would be less damaging, and in part because, during many years, there had been no alternative scalable drying technologies available. Conventional freeze-drying requires a very long time, excessive costs, and in many cases, produces low yields because it is a very damaging process for many biopharmaceuticals. Freeze-dried biopharmaceuticals, such as vaccines, require refrigeration and a cold chain to maintain stability and viability during transportation, storage, and delivery to the point of use. Lyophilization-induced injury happens both during freezing and during subsequent ice sublimation from frozen specimens at intermediate low temperatures (between −50° C. and −20° C.). It is at these temperatures that most damaging cryochemical reactions occur.

Spray Drying

Spray drying has also been unsuccessful in delivering ambient-temperature stable vaccines.

Spray drying is a scalable process for drying of biological specimens sprayed in a dry environment at high temperatures. Conventionally spray drying was used as a sterilization process for milk and other biological liquids during drying. Removal of the water from the small drops (microsphere) during spray drying occurs by evaporation, which is limited by diffusion of the water from the middle of a microsphere to its surface. Characteristic time (t) of the diffusion relaxation in the drop with diameter (d) is about $t=d^2/D$, where D is the water diffusion coefficient. In water, $D=10^{-5}$ sm$^2$/sec and for small drops with diameter d=10μ and t=0.1 sec. However, for drops containing concentrated solutions (syrups), it will greatly increase because D of syrups is smaller than $10^{-5}$ sm$^2$/sec by many orders of magnitude. The solution to slowing the drying with water leaving the drop is increasing the drying temperature, which could damage the vaccine. Here it is important to note that when D becomes very small it will take many hours to remove water even from a micron size particles. This is a major reason explaining why it is very difficult to reach high glass transition temperature after spray-drying without over-heating and destroying the vaccine activity.

Vacuum Foam Drying

Vacuum Foam Drying was introduced to scale up desorption. In brief, the technique of foam drying is composed of boiling a very concentrated and viscous aqueous solution (Syrup) under vacuum at ambient temperature (AT), such that it transforms into foam. During this process shear stresses that occur in the viscous liquid during the growth of vapor bubbles nucleate new bubbles that split thick films into thin films that can quickly dry under vacuum. The large surface area of the foam allows efficient desorption of the water from the bubbling syrup and solidification of the material in the foam; and at the end of the vacuum drying period the solution becomes a mechanically stable dehydrated foam.

Preservation by Vaporization (PBV)

Preservation by Vaporization (PBV) is a core technology for development and production of ambient-temperature stable probiotics, live attenuated vaccines (LAV) and other biopharmaceuticals, and is described in detail in commonly owned WO 2005/117962. PBV is a scalable, reproducible, and automatable state of the art generation of vacuum foam drying that is free from the drawbacks of Preservation by Foam Formation (PFF).

PFF is described in "Preservation by Foam Formation", U.S. Pat. No. 5,766,520 (1998). Additionally, PFF is described in Bronshtein, V. article "Preservation by Foam Formulation, an Alternative to Freeze-Drying" (Pharmaceutical Technology. 28: 88-91, 2004); which describes an alternative to freeze-drying for production of ambient temperature stable vaccines.

PBV can be performed in unit dose format (in vials) and/or in bulk format (in trays, bags, or other containers) using conventional freeze-drying equipment. In addition, PBV could be executed as a barrier continuous load process that is ideal for the production of biopharmaceuticals.

PBV overcomes deficiencies of conventional scalable drying technologies such as freeze-drying and spray-drying. Today foam drying is the only scalable drying technology that has been proven to deliver fragile ambient-temperature stable biologicals like live attenuated vaccines.

Ambient-temperature stable vaccines and other biologicals formed by PBV have a shelf life at ambient temperatures measured in years and are suitable for needle-free delivery using dry powder inhalers, tablets, dissolvable films, microneedle patches, suppositories, ointments, creams, and enteric coated capsules among others, including the embodiments as disclosed herein.

It has been recognized that there is a need for mucosal and transdermal delivery of biopharmaceuticals, especially in regions of the World where professional medical care is limited, for example, in developing countries. With this in mind, there is a significant need for delivery platforms, such that certain biopharmaceuticals can be manufactured, stored, transported, and ultimately administered to a patient, ideally without a syringe delivery platform. Thus, modern solutions containing improvements in the art are necessary to meet these current demands.

SUMMARY OF THE INVENTION

It is one aim of the disclosed embodiments to ameliorate certain problems as described above, wherein an ambient-temperature stable therapeutic composition comprises one or more thermostable inactivated but therapeutically active (IBTA) biopharmaceuticals immobilized in a dry amorphous carbohydrate-glass matrix, where the biopharmaceuticals is inactivated by irradiation in the dry state while they had been already preserved (immobilized) for ambient-temperature storage and distribution without the need for a cold chain.

In another aspect, we propose a method for formulation of a combined therapeutic or vaccine composition containing inactivated but therapeutically active (IBTA) microorganisms and sterilized antigens, therapeutic proteins or other macromolecules. To achieve this, both microorganisms and macromolecules first are immobilized in a carbohydrate glass to ensure stability at AT, and after immobilizing, the microorganisms and macromolecules are subsequently sterilized by irradiation without destroying there therapeutic or immunological activity. The scalable immobilization (stabilization) of biologicals in the carbohydrate glass could be achieved using preservation by vaporization, preservation by foam formation, or any other foam drying technology.

These and other features, embodiments, characteristics and alternatives are further described in the appended detailed description of the preferred embodiments.

BRIEF DESCRIPTION OF THE DRAWINGS

FIG. 1 is a plot illustrating survival of vegetative form of anthrax sterne strain vaccine after PBV drying and subsequent storage at 37° C.

FIG. 2 is a plot illustrating metabolic activity of irradiated with 12.5 kGy anthrax vaccine in accordance with an MTT assay.

FIG. 5 illustrates a method for producing thermostable inactivated but therapeutically active biopharmaceuticals.

DETAILED DESCRIPTION OF THE PREFERRED EMBODIMENTS

Figure 3:
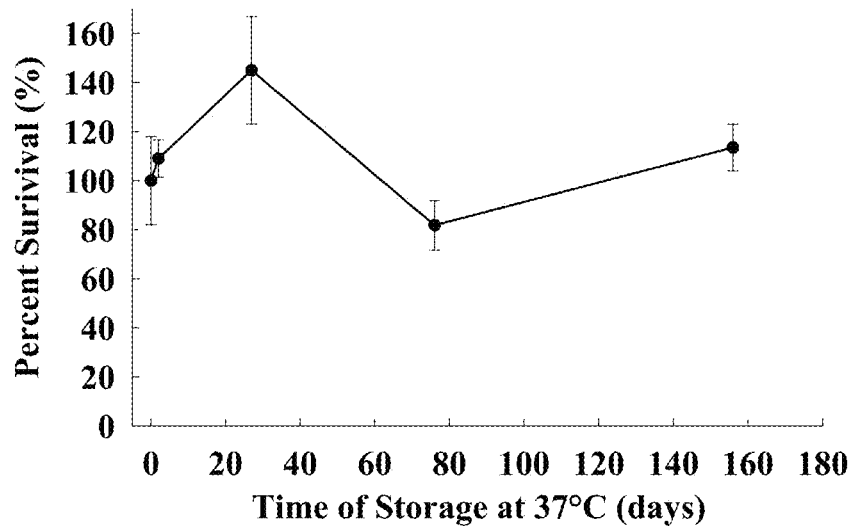
FIG. 3 is a plot illustrating stability of L. Acidophilus after drying and subsequent storing at 37° C.

For purposes of this invention, the terms "foam drying" and "vacuum foam drying" are herein to describe various drying techniques for obtaining preserved materials, including "preservation by foam formulation (PFF)" as described in U.S. Pat. No. 5,766,520; and "preservation by vaporization (PBV)" as described in WO 2005/117962; the contents of each of which are hereby incorporated by reference.

The term "preservation by vaporization (PBV)" describes a current state of the art foam drying technique for preserving sensitive biological material in an amorphous sugar-glass by simultaneous sublimation, evaporation and boiling of water from within a partially frozen slush-state, as is further described in WO 2005/117962.

The terms "carbohydrate-glass" or "sugar-glass" are used herein to describe an amorphous solid carbohydrate matrix including one or more carbohydrates, generally sugars. The matrix may further include amino acids, salts, surfactants and polymers that were dissolved in preservation solutions prior to drying.

In accordance with aspects of the invention, it is a primary objective to provide vaccines and other biopharmaceutical products with improved therapeutic activity, and to enhance methods for formulating such products.

In a general embodiment, a method for formulation of a therapeutic composition containing inactivated but therapeutically active (IBTA) biopharmaceuticals comprises: (i) preserving biopharmaceuticals in a dry state; (ii) irradiating the biopharmaceuticals in the dry state to yield IBTA biopharmaceuticals; and (iii) using the IBTA biopharmaceuticals to form the therapeutic composition.

Preserving the biopharmaceuticals in the dry state can comprise any foam drying technique, including preservation by foam formulation, or preservation by vaporization as referenced above. In each of these techniques, the result is an amount of biopharmaceuticals being stabilized within a dry amorphous carbohydrate-glass matrix.

Although not preferred, it is conceivable that a similar result can be achieved using lyophilization of a biopharmaceuticals suspension; however, at the risk of harming sensitive biomaterial structures of the biopharmaceuticals and thereby reducing therapeutic effectiveness. Other techniques can be similarly implemented for preserving the biopharmaceuticals.

Once stabilized in the dry amorphous carbohydrate-glass matrix, the encapsulated and immobilized biopharmaceuticals are subjected to irradiation. The irradiation ideally comprises electron beam (EB) irradiation, but may alternatively include: Gamma, X-ray, proton, neutron, UV irradiation, or a combination thereof. Although radiation dose can be varied, the radiation dose should be at least 12 kGy in certain embodiments.

Once preserved, and subsequently irradiated, the resulting inactivated but therapeutically active (IBTA) biopharmaceuticals can be further formed into a composition by any of: (i) reconstituting the encapsulated and immobilized IBTA biopharmaceuticals in an aqueous solution, (ii) combining the encapsulated and immobilized IBTA biopharmaceuticals with a dry compound to form a therapeutic mixture, or (iii) micronizing the encapsulated and immobilized IBTA biopharmaceuticals to form a therapeutic powder.

In an embodiment, an amount of first therapeutically active biopharmaceuticals is preserved using a foam drying technique, the first preserved biopharmaceuticals are further inactivated by irradiation in the dry foam state, and subsequently micronized to yield a first preserved biopharmaceutical powder. An amount of second therapeutically active biopharmaceuticals is preserved using a foam drying technique, the second preserved biopharmaceuticals are inactivated by irradiation in the dry foam state, and subsequently micronized to yield a second preserved biopharmaceutical powder. Each of the first and second biopharmaceutical powders are then combined to yield a therapeutic composition, in this case a mixture of distinct preserved and inactivated biopharmaceuticals. Note that the foam drying technique can be any foam drying technique, and is independent for producing each of the first and second powders.

In another embodiment, an amount of first therapeutically active biopharmaceuticals is mixed with an amount of second therapeutically active biopharmaceuticals. The first and second biopharmaceuticals are collectively preserved using a foam drying technique, and further irradiated when in the dry state. The resulting foam is micronized to yield a powder containing inactivated but therapeutically active (IBTA) biopharmaceuticals for biopharmaceutical applications.

Experiments have shown that with biopharmaceuticals immobilized in carbohydrate-glass, electron beam irradiation can be used to reduce the viability of dry preserved bacteria more than one million times with minimal loss of metabolic activity, indicating that the internal bacterial proteins and enzymes are structurally and functionally intact after EB irradiation. In contrast, UV irradiation of cells in the liquid state can result in the formation of highly reactive radicals that can degrade proteins. An important benefit of using EB irradiation to produce vaccines is that radiation in the dry state will damage nucleic acids and not protein antigens on the bacterial surface. EB irradiation of dried biologicals is a simple and inexpensive procedure that does not require addition of psoralen.

In the embodiments herein, it is preferred to first make the biopharmaceuticals ambient-temperature stable by encapsulating in a carbohydrate-glass matrix, and then attenuate them by EB irradiation. This approach enables one to evaluate survival of dry preserved bacteria prior to irradiation, and assess protein integrity after irradiation by measuring metabolic activity instead of performing expensive animal immunogenicity studies.

Compositions containing ambient-temperature stable, inactivated but therapeutically active (IBTA) biopharmaceuticals present a unique opportunity for safe and efficacious treatment options.

It is important to note that primary irradiation in the liquid state produces harmful free radicals that unpredictably damage the biological components. Accordingly, the methods described herein incorporate irradiation in the dry state, after stabilization, which effectively limits production of free radicals, and targets only the nucleic acids required for replication while maintaining the metabolism-associated structures intact.

In contrast, methods which irradiate first and preserve second will fail to retain cellular metabolism. Because they are liquid-irradiated first, all the cells that are subsequently stabilized are preserved in the damaged state with much of their metabolic activity already lost.

Thus, when inactivated properly, appropriate organisms will retain therapeutic potency and be a safer alternative to their live counterparts.

In one embodiment, the step of encapsulating the therapeutically active biopharmaceuticals in a dry amorphous carbohydrate-glass matrix is achieved using the technique known as Preservation by Vaporization (PBV). PBV generally includes: (i) providing the biopharmaceuticals in one of an aqueous solution or a hydrogel to form a first composition; (ii) partially freezing the first composition to form a two-phase state thereof, wherein the first composition comprises an amount of ice and an amount of liquid water in the two-phase state; (iii) vaporizing the first composition, the vaporizing comprising simultaneously applying vacuum and heat, wherein water is removed from the first composition through simultaneous boiling of the liquid, sublimation of ice, and evaporation of water molecules from a surface of the liquid; and continuing the vaporization to transform the first composition into a dry foam, wherein the dry foam forms the carbohydrate-glass matrix that encapsulates the biopharmaceuticals.

Where a hydrogel is incorporated into the first composition, the hydrogel can comprise calcium alginate.

PBV is a current state of the art because the process yields high thermostability without significant disturbance of activity. For this reason, PBV is preferred, however, other foam drying techniques can be similarly implemented to encapsulate the biopharmaceuticals in a dry amorphous carbohydrate-glass matrix, for example, by using the technique known as "preservation by foam formulation (PFF)" as referenced above.

FIG. 5 illustrates a method for producing thermostable inactivated but therapeutically active biopharmaceuticals.

EXAMPLES

Example 1: Preparation of Inactivated but Therapeutically Active (IBTA) Viral Lave Attenuated Vaccine Fixed rabies virus (RV), Evelyn-Rokitnicki-Abelseth (ERA) strain, was attenuated using a reverse genetics system. The recovered virus was sequenced and had only the desired change (R333E). The resulting virus, referred to as ERAg333, was grown.

Supernatant was mixed (1:2) with 30% sucrose and 15% methylglucoside in phosphate buffer (pH=7.0). 0.5 ml of mixture was distributed into crimp vials and dried using Genesis and Virtis Ultra freeze-dryers that were modified to allow better vacuum pressure control. After two hours of processing, the solid material formed a stable dry foam. Secondary drying was performed under vacuum at 35° C. and 45° C. for 20-24 hours. RV preservation by vaporization (PBV) in crimp vials at 22° C. with desiccant was electron beam-irradiated at various doses. Virus titers were measured as described below except in 96-well plates on four consecutive days post infection.

Commercially available RV vaccine RabAvert was purchased and reconstituted according to the manufacturer's instructions.

RV PBV in crimp vials was placed at 22° C. with desiccant, in a dry incubator at 37° C., in mineral oil bath at 80° C. and 90° C. for viability, or in a water bath at 80° C. for electrochemiluminescent (ECL) assays. Vials were removed at different time points and reconstituted with 0.4 ml phosphate buffered saline (PBS) (0.01M, pH 7.4). Virus titers were measured by serially diluting vaccine with BHK-21 cells in an 8-well chamber slide as described previously. The mean focus forming units (ffu)/ml and standard deviation were calculated from at least three statistical replicates.

The Meso Scale Discovery platform was used to perform RV antigen capture ECL assays as described previously. RV glycoprotein (G) monoclonal antibody (MAb) 62-80-6 was used at 1 µg/ml for capture and 0.5 µg/ml for detection.

Approved animal use protocols were established with CDC IACUC. Blood was collected as described previously from female, 4-week-old, CD-1 mice assigned to groups of 10, and the geometric mean titer (GMT) of RV neutralizing antibodies (rVNA) in international units (IU)/ml was determined using a rapid fluorescent focus inhibition test (RFFIT) or a modified RV neutralization test for small volumes. Live attenuated RV PBV vaccine, placebo, and inactivated RV PBV, stored for 36 days at 22° C. in the dark with desiccant, were reconstituted with 0.4 ml of sterile PBS (0.01M, pH 7.4) without calcium or magnesium. Reconstituted vaccine and RV ERAg333 from frozen stock was subsequently diluted using the same PBS. On day 0, mice were vaccinated intramuscularly (IM) in the right leg as described previously. Back titrations of dilutions used to vaccinate mice were completed as described above. For inactivated vaccines, the BCA Protein Assay was used according to manufacturer's instructions to determine total protein concentration. Blood was collected again from all mice on day 14 and 30, and rVNA GMT was determined. On day 30 all mice were challenged IM in the left leg with 50 μl of canine RV 3374R. Animals were monitored and euthanized when showing signs of rabies as described previously. The brain stem was collected from euthanized animals and subjected to the direct fluorescent antibody (DFA) test for rabies. The experiment was terminated 30 days after the last death in the placebo group. Probability values were calculated using chi-square test with a 95% confidence interval.

Results

The starting titer of RV ERAg333 before PBV was 8.3 log 10 ffu/ml. After PBV, about 0.2 log 10 of viable virus was lost resulting in 8.11±0.12 log 10 ffu/ml. For inactivated vaccines, electron beam-irradiation at all tested doses damaged RV and resulted in lower virus titers; no viable virus was recovered in samples treated with the highest dose of 12 kGy (Table 1). The complete inactivation of rabies virus after treatment with 12 kGy was confirmed in three blind cell passages.

TABLE 1

Inactivation of RV PBV by electron beam

| Dose | Rabies virus titer ($log_{10}$ ffu/ml) | | | |
|---|---|---|---|---|
| (kGy) | 24 hrs | 48 hrs | 72 hrs | 96 hrs |
| 0 | 8.16 ± 0.1 | TNC[a] | TNC | TNC |
| 2.9 | 6.03 ± 0.04 | TNC | TNC | TNC |
| 4.2 | 4.82 ± 0.24 | TNC | TNC | TNC |
| 6 | 4.32 ± 0.25 | TNC | TNC | TNC |
| 12 | BLD[b] | BLD | BLD | BLD |

[a]Too numerous to count (TNC)

[b]Below level of detection (BLD); no virus detected

RV PBV was stored at 22° C. with desiccant for 1, 2, 3, 15, or 23 months. After a 0.5 log 10 drop in the first two months, the vaccine was stable up to the end of the experiment, when viability only decreased approximately 0.6 log 10 (Table 2). RV PBV was incubated at 37° C. for 1, 2, 15, or 23 months. After 2 months, viability dropped <1 log 10 and after 15 months dropped 1.5 log 10. RV PBV was placed at 80° C. or 90° C. After 3 hours at 80° C., viability was essentially the same, and only 1 log 10 of viable virus was lost after 16 hours. Incubation at 90° C. was significantly more damaging, and RV PBV lost >1 log 10 of activity after 1 hour at 90° C.

TABLE 2

Viability of RV after PBV and storage at different temperatures
Rabies virus titer ($log_{10}$ ffu/ml)

| Temp. | Initial | 1 hrs | 2 hrs | 3 hrs | 16 hrs | 1 M | 2 M | 3 M | 15 M | 23 M |
|---|---|---|---|---|---|---|---|---|---|---|
| 22° C. | 7.91 ± 0.05 | ND[a] | ND | ND | ND | 7.51 ± 0.07 | 7.40 ± 0.09 | 7.39 ± 0.12 | 7.42 ± 0.04 | 7.33 ± 0.05 |
| 37° C. | 7.56 ± 0.14 | ND | ND | ND | ND | 7.13 ± 0.17 | 6.99 ± 0.01 | ND | 6.1 ± 0.09 | 5.58 ± 0.22 |
| 80° C. | 7.51 ± 0.07 | 7.56 ± 0.09 | 7.48 ± 0.15 | 7.46 ± 0.05 | 6.53 ± 0.05 | ND | ND | ND | ND | ND |
| 90° C. | 7.51 ± 0.07 | 6.07 ± 0.09 | ND | ND | ND | ND | ND | ND | ND | ND |

[a]Not determined (ND)

MAb 62-80-6 was used for capture and detection of RV G in an antigen capture assay and counts μg-1 ml-1 were estimated from the best fit linear regression. In agreement with the measured virus titers, live attenuated RV PBV had the same counts μg-1 ml-1 as the original ERAg333 virus (Table 3).

TABLE 3

Antigenic G content of different RV vaccines measured by antigen capture assay using the 62-80-6 α RV G MAb
Storage Conditions

| Antigen | Time | Temperature | ECL Counts $\mu g^{-1}$ $ml^{-1a}$ |
|---|---|---|---|
| ERAg333[b] | 20 M | −80° C. | 2200 |
| Live attenuated RV PBV | 20 M | 22° C. | 2200 |
| Commercial vaccine | 25 M | 4° C. | 1400 |
| | 3 hrs | 80° C. | 980 |
| Inactivated RV PBV | 20 M | 22° C. | 1300 |
| | 3 hrs | 80° C. | 680 |

TABLE 3-continued Antigenic G content of different RV vaccines measured by antigen capture assay using the 62-80-6 α RV G MAb Storage Conditions

| Antigen | Time | Temperature | ECL Counts $\mu g^{-1}$ $ml^{-1a}$ |
|---|---|---|---|
| Native ERA G[c] | 18 M | −80° C. | 9100 |
| Denatured ERA G[c] | 10 mins | 98° C. | 7 |
| Placebo | 20 M | 22° C. | 3 |

[a]Estimated from the best fit linear regression of means of at least four statistical replicates from at least two biological replicates of eight 5-fold serial dilutions
[b]Parent strain for both live attenuated and inactivated vaccines; generated by reverse genetics
[c]Purified RV ERA glycoprotein Inactivation of RV PBV by electron beam irradiation resulted in a decrease in antigen content but was similar to a commercial inactivated vaccine. When inactivated RV PBV was placed at 80° C. with high humidity for 3 hours, antigen decreased 48% while decreasing 30% in a commercial vaccine incubated under the same conditions.

Live attenuated and inactivated RV PBV was used to vaccinate mice IM. Both live and inactivated RV PBV effectively induced rVNA titers by day 14 (Table 4). Live vaccine induced rVNA titers similar to ERAg333 and commercial vaccine. On day 30 rVNA titers increased in groups that received live RV PBV surpassing ERAg333 and commercial vaccine. Inactivated RV PBV induced rVNA titers on day 30 similar to commercial vaccine on day 14.

The different dilutions of live attenuated RV PBV induced similar rVNA titers on day 14 and 30. Only the undiluted and 10-1 dilution of inactivated RV PBV vaccine induced rVNA titers by day 30. The decreased immunogenicity of the inactivated RV PBV is consistent with the in vitro antigen capture results.

On day 30 all mice were challenged with canine street RV IM in the hind leg. All animals that received commercial vaccine survived (Table 4, p<0.01 compared to placebo). All animals also survived in groups that received ERAg333 or live RV PBV, consistent with the observed rVNA responses. In groups that received inactivated RV PBV all animals survived except in the 10-2 group. In this group, 80% survived despite only 3 individuals having a measurable rVNA response. Survivorship in this group was significantly different compared to the placebo (p<0.05) but not compared to the commercial vaccine or other inactivated RV PBV groups. At the experimental endpoint, animals from each group were randomly selected for rabies diagnosis, and all were rabies DFA negative.

TABLE 4

Immunogenicity and efficacy of rabies vaccine preserved by vaporization in mice

| | Live Attenuated Vaccine | | | ERAg333[a] | Placebo | Commercial Vaccine | Inactivated Vaccine | | |
|---|---|---|---|---|---|---|---|---|---|
| Group | 1 | 2 | 3 | 4 | 5 | 6 | 7 | 8 | 9 |
| Dilution | $10^{-1}$ | $10^{-2}$ | $10^{-3}$ | $10^{-2}$ | None | None | None | $10^{-1}$ | $10^{-2}$ |
| Titer | 6.8[b] | 5.7 | 4.4 | 7.9 | NA[c] | NA | NA | NA | NA |
| Load | ND[d] | ND | ND | ND | 300[e] | 620 | 350 | 34 | 2.3 |
| GMT day 14[f] | 0.26[g] | 0.11 | 0.2 | 0.37 | <0.05 | 0.23 | 0.07 | <0.05 | <0.05 |
| SD day 14[h] | ±0.50[g] | ±0.70 | ±0.95 | ±0.98 | ±0.0097 | ±0.56 | ±0.11 | ±0.24 | ±0.022 |
| GMT day 30[f] | 1.60[g] | 0.96 | 1.7 | 0.84 | <0.05 | 0.58 | 0.27 | 0.13 | 0.05 |
| SD day 30[h] | ±2.4[g] | ±15 | ±2.9 | ±1.9 | ±0.015 | ±1.9 | ±1.4 | ±0.58 | ±0.14 |
| Survival[i] | 100%[j] | 100% | 100% | 100% | 22% | 100% | 100% | 100% | 80%[k] |

[a]Parent strain for both live attenuated and inactivated vaccines; generated by reverse genetics
[b]$Log_{10}$ ffu in 0.1 ml dose
[c]Not applicable (NA); cannot be determined for inactivated vaccines
[d]Not determined (ND)
[e]μg of total protein in 0.1 ml dose
[f]Geometric mean titer (GMT) of rabies virus neutralizing antibodies
[g]IU/ml
[h]Standard deviation (SD) of rabies virus neutralizing antibody titers
[i]Group size = 10 except placebo n = 9
[j]p < 0.01 compared to placebo
[k]p < 0.05 compared to placebo Discussion RV ERAg333 was successfully formulated into stable, dry foam using PBV technology. Live attenuated RV PBV was stable for 23 months at 22° C. and 2 months at 37° C. Stability decreased as temperature increased, yet RV PBV remained stable for at least 3 hours at 80° C.

An antigen capture assay was used to compare the antigen content of different vaccines. Since the ERAg333 virus was used for RV PBV preparation, MAb 62-80-6 which binds a linear epitope in the G was used for both antigen capture and detection. By using the same antibody for capture and detection, only trimeric G is detected. This was confirmed by low ECL counts for heat denatured purified RV G antigen. While the antigen capture assay is not a substitute for potency testing, it can be used to project if vaccines are immunogenic. Live attenuated and inactivated RV PBVs were both antigenic and immunogenic.

A single dose of live attenuated or inactivated RV PBV effectively induced rVNA and protected all mice from IM challenge with a canine RV. By day 30 the antibody response to live attenuated RV PBV surpassed commercial vaccine. Previous challenge experiments using the same RV, dose, and route found 100% mortality in unvaccinated mice. However, the IM challenge, while more closely modeling natural infection, introduces greater variability.

The advantages of PBV are that live attenuated RV can be stabilized and formulated into an oral vaccine suitable for use in domestic or wild animals. These results also support the use of PBV technology for other vaccines, e.g. RV-vectored ebola vaccine. Inactivated RV PBV if formulated into a potent vaccine and paired with a needle-less delivery system could be considered for human use in the future. Access to safe, potent vaccines is paramount for canine rabies elimination and prevention of rabies in humans.

Figure 4:
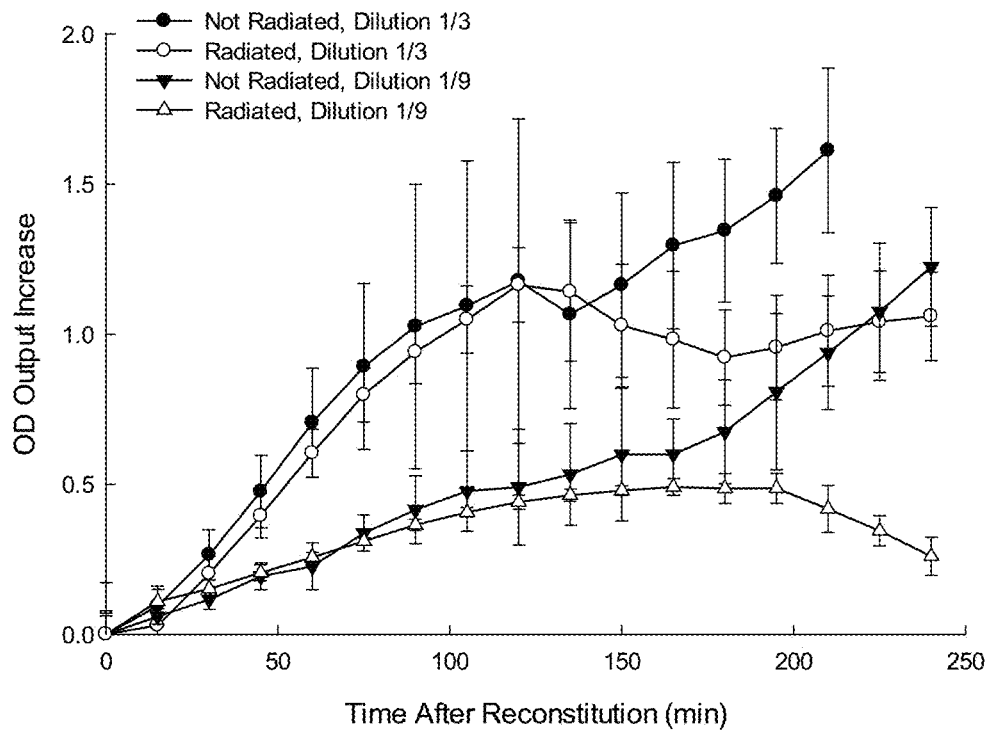
FIG. 4 is a plot illustrating metabolic activity of PBV-preserved L. Acidophilus irradiated with 12.5 kGy.

Example 2: Preparation of Ambient-Temperature Stable, Inactivated but Therapeutically Active (IBTA) Probiotics and Other Bacteria FIGS. 1-4 describe an example including formulation of ambient-temperature stable, inactivated and metabolically active vegetative form of *Bacillus anthracis* and *Lactobacillus acidophilus* bacteria.

*B. anthracis* Sterne strain bacteria were dry preserved using PBV (FIG. 1) and subsequently exposed to electron beam (EB) irradiation. Bacterial survival (CFU) and metabolic (reducing) activity of bacteria were measured using an MTT assay for two hours after the bacteria were reconstituted. A 12.5 kGy dose decreased survival of *B. anthracis* bacteria measured by colony forming units on agar more than one million times with only 0.5 log decrease in metabolic activity during the first hour after reconstitution (FIG. 2). In studies with other PBV-preserved *L. acidophilus* (see FIG. 3) we demonstrated that a 12.5 kGy EB irradiation dose decreased bacterial survival more than a million times with no detectable loss in metabolic activity during the first 1.5 hours after reconstitution (see FIG. 4). These results suggest that EB processing did not damage integrity of bacterial membranes, integrity of the bacterial intermembrane proteins and integrity of intracellular reducing enzymes. Thus EB radiation damages mostly nucleic acids.

What is claimed is:

1. A composition, comprising:
   an amount of inactivated but therapeutically active (IBTA) ERAg333 virus immobilized in a dry amorphous carbohydrate-glass,
   said IBTA ERAg333 virus characterized as being inactivated by irradiation while in the dry state and having a loss of potency less than 0.5 logs after one year of storage at a storage temperature between −20° C. and 37° C., wherein said composition is ambient-temperature stable.

2. The composition of claim 1, wherein the dry amorphous carbohydrate-glass comprises two parts sucrose and one part methylglucoside.

3. The composition of claim 1, wherein the composition is stable for twenty-three months at 22° C.

4. The composition of claim 1, wherein the composition is stable for two months at 37° C.

5. A composition, comprising:
   an amount of inactivated but therapeutically active (IBTA) ERAg333 virus immobilized in a dry amorphous carbohydrate-glass, the carbohydrate-glass comprising two-parts sucrose and one-part methylglucoside,
   said IBTA ERAg333 virus characterized as being inactivated by irradiation while in the dry state and having a loss of potency less than 0.5 logs after one year of storage at a storage temperature between −20° C. and 37° C.

* * * * *